United States Patent
Orlowski et al.

(10) Patent No.: US 6,284,030 B1
(45) Date of Patent: Sep. 4, 2001

(54) SALIVA CURED ONE COMPONENT DENTAL FORMULATIONS

(75) Inventors: Jan A. Orlowski, Altadena; David V. Butler, West Covina, both of CA (US)

(73) Assignee: Scientific Pharmaceuticals, Inc, Pomona, CA (US)

( * ) Notice: Subject to any disclaimer, the term of this patent is extended or adjusted under 35 U.S.C. 154(b) by 0 days.

(21) Appl. No.: 09/408,000

(22) Filed: Sep. 29, 1999

(51) Int. Cl.$^7$ ...................................................... A61K 6/00
(52) U.S. Cl. .......................... 106/35; 433/228.1; 523/116
(58) Field of Search .............................. 106/35; 523/116; 433/228.1

(56) References Cited

U.S. PATENT DOCUMENTS

| | | | | |
|---|---|---|---|---|
| 3,837,865 | * | 9/1974 | Pellico .................................... | 106/35 |
| 4,518,430 | | 5/1985 | Brown et al. ........................... | 106/35 |
| 4,612,053 | | 9/1986 | Brown et al. ........................... | 106/35 |
| 5,051,130 | * | 9/1991 | Futami et al. .......................... | 106/35 |
| 5,108,506 | * | 4/1992 | Yuhda et al. ........................... | 106/35 |
| 5,154,613 | * | 10/1992 | Cohen ................................. | 433/228.1 |
| 5,569,308 | | 10/1996 | Sottosanti ............................ | 623/125 |
| 6,028,125 | * | 2/2000 | Combe et al. ....................... | 523/116 |

* cited by examiner

Primary Examiner—C. Melissa Koslow
(74) Attorney, Agent, or Firm—Knobbe Martens Olson & Bear, LLP

(57) ABSTRACT

A one-component paste-consistency dental material which cures upon contact with oral fluids intended primarily for use as a temporary restorative/cement. The formulation includes solid particles reactive with water dispersed in a hydrophobic viscous binder which, upon exposure to moisture, will solidify to a depth in excess of 8 mm measured from the surface/water contact area. The curing mechanism relies on both formation of hydrates and reaction of organic polyacids with alkaline glass or metal oxides, or the salts of metal oxides with weak acids. The resulting cured material is non toxic, resistant to deterioration in oral fluids, possesses adequate water resistance, and, optionally, may release fluoride desirable for prevention of secondary decays and alleviation of postoperative tooth sensitivity.

20 Claims, No Drawings

SALIVA CURED ONE COMPONENT DENTAL FORMULATIONS

BACKGROUND OF THE INVENTION

This invention relates to a novel dental temporary filling material/cement comprising an inert viscous hydrophobic matrix in which fine solid particles are dispersed such that, upon reaction with water and/or certain organic polyacids, the physical form of such blend is transformed from that of a moldable paste to a solid. The high concentration of hydrophilic solid particles ensures water conductivity through the mass of the material. Such moisture penetration is critical to achieve a satisfactory depth of cure, as measured as a distance from the saliva/restoration borders.

In this invention, the role of the dispersed solid particles is, therefore, of dual nature:

- As components responsible for the cure of the cement and its final mechanical properties, and
- As moisture conductors through the mass of the restoration.

The curing of the materials of this invention occurs as a result of two types of chemical processes occurring simultaneously:

- Reaction of salts and/or oxides with water or formation, of adducts of salts and waters, and
- Reaction of alkaline glass sites with polyacids, or the reaction of such polyacids with metal oxides, hydroxides, or salts of such materials, with weak organic acids.

The chemical composition of the formulations of this invention resulted in cements featuring highly desirable characteristics. These materials were found particularly suitable for use as temporary restoratives and cements where the ease and speed of application, fast cure, resistance to the oral environment, biological mildness, and ease of removal are of primary concern. Astonishingly, it was further realized that the formulations of this invention, contrary to those of the prior art, show no or minimal volumetric expansion during cure—a feature of critical importance for dental restoratives and cements. An additional advantage is that sustained fluoride release can easily be implemented without negatively affecting the characteristics or the integrity of the restorative.

DESCRIPTION OF PRIOR ART

Known dental restoratives an cements may be separated by their method of cure into three groups:

- Self cured materials, usually representing a two part system in which the curing process is initiated by mixing the two components;
- Light cured materials, usually a one part system in which the curing process is initiated by irradiation with high intensity light; and
- Saliva cured materials, in which curing occurs as a result of hydration of inorganic components of the formulations.

While the first two types are primarily used for permanent dental restorations, the third is limited to temporary applications where short service time, typically of less than seven days, is reasonably expected.

Important features of materials for temporary applications, as dictated by both clinical and economical considerations include easy and fast application, short curing time, low cost, long shelf life, adequate depth of cure, biocompatibility, resistance to oral fluids, adequate mechanical strength, ease of removal, and compatibility with permanent restoratives and cements.

Prior art saliva cured-type temporary restoratives/cements were generally inadequate in many respects. The curing time was slow, making the material vulnerable to premature deterioration, especially during the hours immediately after application. The curing of the material progressed very slowly, and was frequently limited to a layer within a few millimeters of the material/saliva borders. Poor resistance to mastication forces, wear, and oral fluids resulted in excessive premature deterioration of the restorations or structural failures.

The present invention addresses the shortcomings of such prior art materials. The addition of a secondary curing mechanism of polyacid salt formation to the hydrate formation mechanism of the prior art allows for faster curing and greatly increased strength. The presence in this invention of initially hydrophilic but reactive components such as anhydrous polyacids facilitates penetration of moisture through them mass of uncured material, thus enhancing the depth and speed of cure.

The material of this invention features greatly increased depth of cure, improved resistance to oral fluids, and superior mechanical strength. These desirable characteristics were achieved while meeting other pertinent requirements, including biocompatibility, ease of application, long shelf life, ease of removal and compatibility of residues with all known dental restoratives and cements.

DETAILED DESCRIPTION OF THE INVENTION

The dental formulation embodying the present invention which cures upon contact with saliva includes a hydrophobic matrix component, an inorganic particles component and an anhydrous acid component.

The preferred hydrophobic organic matrix for the dental cement formulations of this invention comprise an organic material of viscous liquid or semi-solid consistency such as fatty acids or their esters, polyalkalenes, mineral oils, paraffins, synthetic or natural waxes, and silicone oils. Polyalkalenes and paraffins were found to be the most suitable matrices.

The reactive inorganic solid particles which contribute, in part, to the hardening of the cement formulation may include calcium sulfate, calcium sulfate hemihydrate, calcium silicate, calcium oxide, magnesium oxide, magnesium chloride, phosphate salts, colloidal silicic acid and certain organosilicone components such as alkoxysilicones. Solid inorganic particles which further contribute to the hardening of the cement, and the substantial improvement in characteristics of the cured material, include, in addition to those mentioned above which contribute to hardening by reaction with water, alkaline glasses, zinc oxide, calcium silicate, calcium hydroxide, and magnesium silicate. Alkaline glasses and zinc oxide are the most preferred of such additional additives.

The inorganic particles which contribute to the hardening of cement, namely calcium sulfate ($CaSO_4$) or calcium sulfate hemihydrate ($CaSO_4 \cdot \frac{1}{2}H_2O$) are present in concentrations of from about 10 to 55% by weight of the formulation.

The inorganic particles component may also include from 2 to about 15% by weight of the formulation calcium phosphate salts such as $CaHPO_4$, $Ca_8H_2(PO_4)_6$, $Ca_3(PO_4)_2$ and/or hydrates thereof.

Additionally inorganic particles reactive with organic particles such as zinc oxide, calcium oxide, calcium hydroxide, magnesium oxide, barium oxide, strontium oxide, calcium carbonate, calcium silicate, magnesium silicate and/or zinc carbonate are suitable for the invention.

The anhydrous acid, polyacid or acid anhydride is preferably a polyacrylic acid, and has on average molecular weight ranging from 2,000–250,000.

The formulation may also include, if desired, additives which affect the appearance of the material. The additives are preferably dyes or pigments which are used to enhance the aesthetics and to facilitate distinction of the cement from tooth structure. Preferred dyes or pigments are iron oxides or titanium dioxide.

It is also envisioned to add, if desired, fluoride releasing salts to the formulation. Salts such as sodium fluoride, stannous fluoride, potassium fluorosilicate, sodium fluorosilicate, zinc hexafluorosilicate or sodium monofluoro phosphate are preferred.

The organic acid is selected from polyacrylic, itaconic, tartaric, citric, maleic, oxalic or lactic acids or their copolymers. Such acids are present in anhydrous form in the formulations of this invention, preferably at concentrations of 1–20% of by weight in the cement. Their reaction with alkaline particles is triggered by the presence of water.

EXAMPLES

The invention is illustrated by the following examples, the purpose of which is to facilitate the understanding of the principles of the invention without, however, limiting its scope as outlined in the claims.

Example 1

This example represents a typical prior art formulation, and is given for reference only.

| Components | % by weight |
|---|---|
| calcium sulfate hemihydrate | 45.60 |
| calcium sulfate anhydrous | 16.67 |
| mineral oil | 10.98 |
| zinc oxide | 10.18 |
| polybutene | 8.28 |
| hydroxyapatite | 4.50 |
| silica | 3.19 |
| potassium sulfate | 0.60 |

Laboratory Testing

Under simulated oral conditions which corresponded to those of a large Class I restoration, this formulation hardened to a depth of approximately 3 mm after 20 hours of exposure. The material on the surface could be easily scratched with a dull plastic instrument. Substantial disintegration of the cured material was observed, as evidenced by the heavy haze of the stirred liquid in which the specimen was suspended.

Example 2

This example represents a saliva cured restorative of this invention in its initial stages of development.

| Components | % by Weight |
|---|---|
| calcium sulfate hemihydrate | 40.64 |
| mineral oil | 29.93 |
| calcium sulfate anhydrous | 18.22 |
| silica | 3.50 |
| zinc oxide | 3.50 |
| alkaline glass | 3.21 |
| polyacrylic acid (average molecular weight ca. 50,000 | 1.00 |

Laboratory Testing

This material, when tested as described in Example 1, was discovered to represent a significant improvement over the previous formulation. The depth of cure increased to over 4 mm. It was, however, easily scratched with a dull plastic instrument. The liquid environment was observed to be hazy.

Example 3

| Components | % of Weight |
|---|---|
| calcium sulfate hemihydrate | 41.67 |
| petroleum jelly | 28.00 |
| calcium sulfate anhydrous | 18.69 |
| silica | 3.58 |
| zinc oxide | 3.58 |
| alkaline glass | 3.38 |
| polyacrylic acid (average molecular weight ca. 50,000 | 1.10 |

Laboratory Testing

This material, when tested as described in Example 1, represented an improvement over the former one. The surface was harder and there was significantly less haze observed in the liquid environment.

Example 4

| Components | % of Weight |
|---|---|
| calcium sulfate hemihydrate | 52.52 |
| mineral oil | 24.77 |
| calcium sulfate anhydrous | 13.46 |
| alkaline glass | 3.09 |
| silica | 2.59 |
| zinc oxide | 2.59 |
| polyacrylic acid (average molecular weight ca. 50,000 | 0.98 |

Laboratory Testing

This material, when tested as described in Example 1, demonstrated significant improvement over the material of Example 3. The surface was satisfactorily hard, i.e. no indention was left after it was pressed with a dull plastic instrument, and only medium haze was observed in the liquid environment.

Example 5

| Components | % of Weight |
| --- | --- |
| calcium sulfate hemihydrate | 50.67 |
| petroleum jelly | 24.94 |
| calcium sulfate anhydrous | 12.99 |
| polyacrylic acid (average molecular weight ca. 180,000 | 3.43 |
| alkaline glass | 2.99 |
| silica | 2.49 |
| zinc oxide | 2.49 |

Laboratory Testing

This material, when tested as described in Example 1, exhibited a depth of cure in excess of 10 mm (the thickness of the specimen). The surface was hard, i.e. no indentation was left when pressed with a dull plastic instrument, and virtually no haze was observed in the liquid environment. In addition, the sample demonstrated minimal volumetric expansion upon curing.

Example 6

| Components | % of Weight |
| --- | --- |
| calcium sulfate hemihydrate | 48.45 |
| petroleum jelly | 24.75 |
| calcium sulfate anhydrous | 10.31 |
| alkaline glass | 5.49 |
| polyacrylic acid (average molecular weight ca. 180,000 | 3.79 |
| zinc oxide | 3.09 |
| calcium oxide | 2.06 |
| calcium silicate | 2.06 |

Laboratory Testing

This material, when tested as described in example 1, exhibited a depth of cure and surface hardness comparable to that of Example 5. No haze was observed in the liquid environment, which was almost clear. In addition, the sample demonstrated minimal volumetric expansion upon curing.

Example 7

| Components | % of Weight |
| --- | --- |
| calcium sulfate hemihydrate | 48.45 |
| petroleum jelly | 21.14 |
| calcium sulfate anhydrous | 10.31 |
| alkaline glass | 5.49 |
| polyacrylic acid (average molecular weight ca. 180,000 | 3.79 |
| silicon oil | 3.61 |
| zinc oxide | 3.09 |
| calcium oxide | 2.06 |
| calcium silicate | 2.06 |

Laboratory Testing

This material, when tested as described in Example 1, exhibited a depth of cure and surface hardness similar to the demonstrated by Examples 5 and 6. Very little haze was observed in the liquid environment. This sample also demonstrated no apparent volumetric expansion upon curing.

It should be understood that the above description discloses specific embodiments of the present invention and are for purposes of illustration only. There may be other modifications and changes obvious to those of ordinary skill in the art which fall within the scope of the present invention which should be limited only by the following claims and their legal equivalents.

What is claimed is:

1. A dental formulation curing upon contact with oral fluids that comprises:

a) hydrophobic organic matrix of fluid or semi-solid, viscous consistency;

b) inorganic particles suspended in the hydrophobic organic matrix; and c) an anhydrous acid, polyacid or acid anhydride wherein the formulation is a single component mixture which cures upon exposure to moisture in oral fluids.

2. The dental formulation as claimed in claim 1, wherein the hydrophobic organic matrix comprises mineral oils, natural and synthetic waxes, polyalkalenes, paraffins, petrolatum, fatty acids and their esters, silicone oils, or mixtures thereof.

3. The dental formulation as claimed in claim 1, wherein the inorganic particles comprises from about 10–55% of weight calcium sulfate ($CaSO_4$) or calcium sulfate hemihydrate ($CaSO_4.\frac{1}{2}H_2O$).

4. The dental formulation as claimed in claim 2, wherein the inorganic particles comprises 2 to about 15% by weight of calcium phosphate salts selected from the group consisting of $CaHPO_4$, $Ca_8H_2(PO_4)_6$, $Ca_3(PO_4)_2$ and hydrates thereof.

5. The dental formulation as claimed in claim 1, wherein the inorganic particles reactive with the acids are selected from the group consisting of zinc oxide, calcium oxide, calcium hydroxide, magnesium oxide, barium oxide, strontium oxide, calcium carbonate, calcium silicate, magnesium silicate, and zinc carbonate.

6. The dental formulation as claimed in claim 1, where the anhydrous acid is polyacrylic acid, having an average molecular weight of 2,000–250,000.

7. The dental formulation as claimed in claim 1, wherein the anhydrous acid comprises tartaric acid, citric acid, itaconic acid, oxalic acid, maleic acid, lactic acid; mixtures thereof, or copolymers with a polyacrylic acid.

8. The dental formulation as claimed in claim 1, further comprising additives which affect the appearance of the material.

9. The dental formulation as claimed in claim 8, wherein the additive is a dye or pigment to enhance esthetics or facilitate tooth structure distinction.

10. The dental formulation as claimed in claim 8 wherein the additive is titanium dioxide or iron oxide.

11. The dental formulation as claimed in claim 1, further comprising a fluoride-releasing salt.

12. The dental formulation as claimed in claim 11, wherein the fluoride-releasing salt is selected from the group consisting of sodium fluoride; stannous fluoride, sodium fluorosilicate, potassium fluorosilicate, zinc hexa fluorosilicate; and sodium monofluoro phosphate.

13. The dental formulation as claimed in claim 1, wherein the anhydrous acid is present from 1 to 20% by weight of the formulation.

14. A dental formulation, comprising:
   a stable mixture comprising a hydrophobic organic compound, a reactive inorganic compound, and an anhydrous acid, polyacid or acid anhydride, wherein the curing of the mixture is initiated by the presence of water.

15. The dental formulation as claimed in claim 14, wherein the hydrophobic organic matrix comprises minerals oils, natural and synthetic waxes, polyalkalenes, paraffins, petrolatum, fatty acids and their esters, silicone oils, or mixtures thereof.

16. The dental formulation as claimed in claim 14, wherein the inorganic particles comprises from about 10–55% of weight calcium sulfate or calcium sulfate hemihydrate ($CaSO_4 \cdot \frac{1}{2}H_2O$).

17. The dental formulation as claimed in claim 14, wherein the inorganic particles comprises from 2 to about 15% by weight of calcium phosphate salts selected from the group consisting of $CaHOP_4$, $Ca_8H_2(PO_4)_6$, $Ca_3(PO_4)_2$ and hydrates thereof.

18. The dental formulation as claimed in claim 14, wherein the inorganic particles reactive with the acids are selected from the group consisting of zinc oxide, calcium oxide, calcium hydroxide, magnesium oxide, barium oxide, strontium oxide, calcium carbonate, calcium silicate, magnesium silicate, and zinc carbonate.

19. The dental formulation as claimed in claim 14, where the anhydrous acid is polyacrylic acid, having an average molecular weight of 2,000–250,000.

20. A dental material comprising:
   a one component formulation comprising
   a hydrophobic organic compound selected from the group consisting of minerals oils, natural and synthetic waxes, polyalkylenes, paraffins, petrolatum, fatty acids, fatty acid esters, silicone oils, and mixtures thereof;
   an inorganic material selected from the group consisting of calcium sulfate, calcium sulfate hemihydrate, calcium silicate, calcium oxide, calcium hydroxide, calcium silicate, calcium hydroxide, calcium phosphate salts, calcium carbonate, calcium silicate, magnesium chloride, magnesium oxide, magnesium silicate, phosphate salts, colloidal silicic acid, alkoxysilicones, alkaline glasses, zinc carbonate, zinc oxide, barium oxide, strontium oxide, and mixtures thereof; and
   an anhydrous acid selected from the group consisting of tartaric acid, citric acid, itaconic acid, oxalic acid, maleic acid, lactic acid, polyacrylic acid, polyacrylic acid copolymers, and mixtures thereof;
   wherein said formulation cures upon exposure to saliva or moisture.

* * * * *